United States Patent
Gordon et al.

(10) Patent No.: US 12,239,680 B2
(45) Date of Patent: Mar. 4, 2025

(54) SLEEP DISORDER COMPOSITIONS AND TREATMENTS THEREOF

(71) Applicant: ZELIRA THERAPEUTICS OPERATIONS PTY LTD, Perth (AU)

(72) Inventors: Mara Gordon, Bodega Bay, CA (US); Stewart Smith, Bodega Bay, CA (US); Stewart Washer, Stirling (AU); Patrizia Washer, Stirling (AU); Harry Karelis, Perth (AU)

(73) Assignee: Zelira Therapeutics Operations Pty Ltd, Perth (AU)

(*) Notice: Subject to any disclaimer, the term of this patent is extended or adjusted under 35 U.S.C. 154(b) by 0 days.

(21) Appl. No.: 18/171,983

(22) Filed: Feb. 21, 2023

(65) Prior Publication Data

US 2023/0270808 A1 Aug. 31, 2023

Related U.S. Application Data

(62) Division of application No. 16/623,525, filed as application No. PCT/AU2018/050604 on Jun. 19, 2018.

(30) Foreign Application Priority Data

Jun. 19, 2017 (AU) ................................ 2017902338
Nov. 29, 2017 (AU) ................................ 2017904818

(51) Int. Cl.
| | | |
|---|---|---|
| A61K 36/185 | (2006.01) | |
| A61K 9/00 | (2006.01) | |
| A61K 31/01 | (2006.01) | |
| A61K 31/045 | (2006.01) | |
| A61K 31/05 | (2006.01) | |
| A61K 31/352 | (2006.01) | |
| A61P 25/20 | (2006.01) | |

(52) U.S. Cl.
CPC ............ *A61K 36/185* (2013.01); *A61K 9/006* (2013.01); *A61K 31/01* (2013.01); *A61K 31/045* (2013.01); *A61K 31/05* (2013.01); *A61K 31/352* (2013.01); *A61P 25/20* (2018.01)

(58) Field of Classification Search
None
See application file for complete search history.

(56) References Cited

U.S. PATENT DOCUMENTS

| | | |
|---|---|---|
| 6,949,582 B1 | 9/2005 | Wallace |
| 8,895,078 B2 | 11/2014 | Mueller |
| 9,649,349 B1 | 5/2017 | Tucker et al. |
| 2015/0086653 A1 | 3/2015 | Parolaro et al. |
| 2016/0106705 A1* | 4/2016 | Verzura ............... A61K 31/353 514/568 |
| 2016/0151328 A1 | 6/2016 | Doane et al. |
| 2016/0346339 A1 | 12/2016 | Finley et al. |
| 2022/0202767 A1 | 6/2022 | Karelis et al. |
| 2022/0218650 A1 | 7/2022 | Karelis |
| 2023/0218566 A1 | 8/2023 | Hopkins et al. |
| 2023/0364052 A1 | 11/2023 | Karelis |
| 2023/0404944 A1 | 12/2023 | Takechi et al. |
| 2023/0414559 A1 | 12/2023 | Karelis et al. |

FOREIGN PATENT DOCUMENTS

| | | |
|---|---|---|
| CN | 103355391 | * 10/2013 |
| CN | 105010577 | 11/2015 |
| EP | 1802274 A1 | 7/2007 |
| ES | 2313414 T3 | 3/2009 |
| WO | 2004016277 A2 | 2/2004 |
| WO | 2013165251 A1 | 11/2013 |
| WO | 2014100231 A1 | 6/2014 |
| WO | 2014/200350 A1 | 12/2014 |
| WO | 2015065544 A1 | 5/2015 |
| WO | 2015068052 A1 | 5/2015 |
| WO | 2015200049 A1 | 12/2015 |
| WO | 2016030369 A1 | 3/2016 |
| WO | 2016/064987 A1 | 4/2016 |
| WO | 2016123475 | 4/2016 |
| WO | 2016094810 A2 | 6/2016 |
| WO | 2016138505 A1 | 9/2016 |
| WO | 2016191651 A1 | 12/2016 |
| WO | 2018011808 A1 | 1/2018 |
| WO | 2018/023163 A1 | 2/2018 |
| WO | 2018173049 A1 | 9/2018 |
| WO | 2019152736 A1 | 8/2019 |

(Continued)

OTHER PUBLICATIONS

Hamajima et al. *Yakugaku Zasshi*, "Sex Difference in the Effects of Tetrahydrocannabinol and Cannabidiol on Pentobarbital-Induced Sleeping Time . . ." 1983, vol. 103, No. 12, pp. 1289-1297.

(Continued)

*Primary Examiner* — Michael V Meller
(74) *Attorney, Agent, or Firm* — Armstrong Teasdale LLP

(57) ABSTRACT

The invention relates to a pharmaceutical composition comprising a *Cannabis* extract and optionally one or more pharmaceutically acceptable carriers, diluents, adjuvants, excipients or any combination thereof, the *Cannabis* extract comprising a cannabinoid fraction comprising $\Delta^9$-Tetrahydrocannabinol (THC), Cannabidiol (CBD), and Cannabinol (CBN) and a terpene fraction in an amount of at least 3% by weight of the extract. The invention also relates to methods of treating sleep disorders using this pharmaceutical composition.

8 Claims, No Drawings

(56) References Cited

FOREIGN PATENT DOCUMENTS

WO    2019178088 A1    9/2019
WO    2013057487 A1    4/2023

OTHER PUBLICATIONS

Australian Examination Report No. 1 dated Jul. 19, 2023.
Japanese Pre-Appeal Report dated Jun. 13, 2023.
International Search Report and Written Opinion for PCT Application No. PCT/AU2018/050604, mailed Aug. 9, 2018 (12 pages).
Russo et al., "Cannabis, Pain, and Sleep: Lessons from Therapeutic Clinical Trials of Sativex®, a Cannabis-Based Medicine," Chemistry and Biodiversity, vol. 4, pp. 1729-1743 (2007).
Hash Oil, Wikipedia, Sep. 16, 2016, (XP055303371), 4 pages.
(Apr. 17, 2017) Myrcene: An Abundant Terpene with Surprising Properties, Royal Queen Seeds, 1 page.
Opposition 2 Writ 1 filed by Unimed del Peru S.A. on corresponding Peruvian Patent Application 002553-2019, Mar. 15, 2021, 10 pages.
Opposition Writ 1 filed by Unimed del Peru S.A. on corresponding Peruvian Patent Application 002553-2019, mailed on Jan. 25, 2021, 94 pages (47 pages in English Language & 47 pages in Foreign language).).
Babson et al. (Apr. 2017) "Cannabis, Cannabinoids, and Sleep: a Review of the Literature", Current Psychiatry Reports, 23, 19:12 pages.
Murillo-Rodríguez et al. (May 2014) "Potential Effects of Cannabidiol as a Wake-Promoting Agent", Current Neuropharmacology, 12(3):269-272.
Shannon et al. (2016) "Effectiveness of Cannabidiol Oil for Pediatric Anxiety and Insomnia as Part of Posttraumatic Stress Disorder. A case Report", Fall, 20(4):8 pages.
Vale et al. (Jan. 2000) "Central Effects of Citral, Myrcene and Limonene, Constituents of Essential Oil Chemotypes from Lippia Alba (Mill.) N.E. Brown", Phytomedicine: International Journal of Phytotherapy and Phytopharmacology, 9(8):709-714.
Office Action in corresponding Israeli Application No. 271503, dated Jun. 9, 2022; English translation; 8 pages.
Merriam Webster, Essential Oil Definition of Essential Oil by Merriam Webster, 11 pages, 2021.
Fishdeck, et al., Cannabinoid Receptor 1 Binding Activity and quantitative analysis of *Cannabis sative* L. Smoke and Vapor. Chem & Pharma Bulletin (2010).
Russo et al., "Taming THC: potential cannabis synergy and phytocanabinoid-terpenoid entourage effects", British Journal of Pharmacology, 2011, 163, 1344-1364.

\* cited by examiner

SLEEP DISORDER COMPOSITIONS AND TREATMENTS THEREOF

FIELD

The invention relates to a method for treating a sleep disorder. The invention also relates to a pharmaceutical composition comprising an extract from a *Cannabis* plant, and its use in the treatment of the sleep disorder.

BACKGROUND

The biological activity of *Cannabis* is well known, and has led it to become a "recreational" drug. However, with the discovery of a class of cannabinoid (CB) receptors, and the relaxation of laws regulating *Cannabis* use—in some jurisdictions decriminalisation—there now exists the opportunity to explore the potential of *Cannabis* as a source of new therapeutics.

There is also a growing movement of patients suffering from chronic diseases, such as sleep disorders, to seek natural remedies as alternative or complementary therapy.

Accordingly, there is a continuing need to develop new treatments for sleep disorders, which are derived, at least in part, from a natural source.

SUMMARY

The invention provides a method of treating a sleep disorder comprising administering to a patient in need thereof an effective amount of a pharmaceutical composition comprising a *Cannabis* extract. Accordingly, also provided is a pharmaceutical composition comprising the *Cannabis* extract and optionally one or more pharmaceutically acceptable carriers, diluents, adjuvants, excipients or any combination thereof.

The *Cannabis* extract comprises a cannabinoid fraction and a terpene fraction. The cannabinoid fraction typically comprises as the primary cannabinoid $\Delta^9$-Tetrahydrocannabinol (THC). The cannabinoid fraction may also comprise one or more further cannabinoids including Cannabidiol (CBD) and Cannabinol (CBN). The terpene fraction typically comprises beta-myrcene, linalool and nerolidol. Preferably the *Cannabis* extract does not contain (or contains very low levels, such as not more than about 0.001 wt %) $\Delta^9$-Tetrahydrocannabivarin (THCV), alpha-pinene or beta-pinene, terpinolene, caryophyllene, humulene and limonene.

In a further aspect, there is provided use of the *Cannabis* extract in the preparation of a medicament for treating a sleep disorder.

In yet another aspect, there is provided a pharmaceutical composition for treating a sleep disorder, wherein the pharmaceutical composition comprises a *Cannabis* extract and optionally one or more pharmaceutically acceptable carriers, diluents, adjuvants, excipients or any combination thereof.

DESCRIPTION OF EMBODIMENT(S)

The present invention provides a pharmaceutical composition comprising a *Cannabis* extract and optionally one or more pharmaceutically acceptable carriers, diluents, adjuvants, excipients or any combination thereof.

*Cannabis* plants produce a diverse array of secondary metabolites, including cannabinoids, terpenes and terpenoids, sterols, triglycerides, alkanes, squalenes, tocopherols, carotenoids and alkaloids. The mix of these secondary metabolites varies depending on several factors, including *Cannabis* variety, part of the *Cannabis* plant extracted, method of extraction, processing of the extract, and season.

There are several varieties of *Cannabis* plant, which have been described under two distinct naming conventions. One of these conventions identifies three distinct species of *Cannabis* plant, namely *Cannabis sativa Linnaeus*, *Cannabis indica* LAM., and *Cannabis ruderalis*. Another convention identifies all *Cannabis* plants as belonging to the *Cannabis sativa* L. species, with the various varieties divided amongst several subspecies, including: *Cannabis sativa* ssp. *sativa* and ssp. *indica*. As used herein, the term "*Cannabis*" refers to any and all of these plant varieties.

The extracts may be formed from any part of the *Cannabis* plant containing cannabinoid, terpene and terpenoid compounds. Extracts may be formed by contacting an extractant with a leaf, seed, trichome, flower, keif, shake, bud, stem or a combination thereof. In some embodiments, the extract is formed from the flowers and shake of a *Cannabis* plant. Suitable extractants include, for example, alcohols (e.g., methanol, ethanol, propanol, butanol, propylene glycol, etc.), water, hydrocarbons (e.g., butane, hexane, etc.), oils (e.g., olive oil, vegetable oil, essential oil, etc.), a solvent (e.g., ethyl acetate, polyethylene glycol, etc.) or a supercritical fluid (e.g., liquid $CO_2$).

The extractant may be completely or partially removed prior to incorporation of the *Cannabis* extract into the pharmaceutical composition, or it may be included in the pharmaceutical composition as a carrier. The extractant may be removed by heating the extract optionally under reduced pressure. In some embodiments, the pharmaceutical composition comprises a residual amount of an extractant (such as ethanol). In some embodiments, the residual amount of extractant may be up to about 10 mg/g or about 5 mg/g. It will be appreciated that some of the more volatile plant metabolites (such as terpenes) may also be removed with the extractant. Accordingly, in some embodiments, removing the extractant may enrich the cannabinoid fraction of the extract.

The *Cannabis* extract comprises a cannabinoid fraction comprising $\Delta^9$-Tetrahydrocannabinol (THC), Cannabidiol (CBD), and Cannabinol (CBN). Of these cannabinoids, THC and CBD do not occur in significant concentrations in *Cannabis* plant material and are formed during the extraction process through decarboxylation of corresponding carboxylic acid derivatives of these cannabinoids (or cannabinoid acids), which are biosynthesised by the *Cannabis* plant. The precise concentration of neutral THC or CBD in a *Cannabis* plant is difficult to quantify due to the potential for decarboxylation of the corresponding cannabinoid acids during analysis. Accordingly, when the pharmaceutical compositions of the invention comprise THC or CBD derived from a Natural source, the composition comprises decarboxylated THC or CBD.

The extraction process typically comprises a decarboxylation step. Decarboxylation refers to the loss of a carboxyl group during conversion of a carboxylic acid derivative of a cannabinoid into the cannabinoid itself. $\Delta^9$-Tetrahydrocannabinolic acid (THC-A) and cannabidiolic acid (CBD-A) are not thermally stable and may be decarboxylated by exposure to light or heat. Some studies have also shown that THC-A and CBD-A can be decarboxylated upon exposure to cofactors or certain solvents. Typically, decarboxylation is carried out by heating the extract in the presence of extractant to a temperature of at least 60° C. (e.g. at least 80° C.). This heating step may be maintained for 30 minutes or longer. In some embodiments, the decarboxylation occurs during extractant removal.

In addition, THC has been shown to oxidise to cannabinol (CBN) when exposed to oxygen and light, including during decarboxylation. Accordingly, in some embodiments, the extraction comprises exposing the extract to light under an oxygen atmosphere. In other embodiments, the extraction is carried out in the absence of oxygen, for example under an atmosphere of nitrogen.

In some embodiments, the extract is filtered to remove particulate material, for example, by passing the extract through filter paper or a fine sieve (e.g., a sieve with pore sizes of 5 µm). The *Cannabis* composition may comprise up to about 5% by weight (e.g., up to about 2% by weight) visible particles.

In some embodiments, the *Cannabis* extract is formed by applying heat and pressure to the plant material. Typically, in these embodiments, no extractant is required.

In some embodiments, the *Cannabis* extract is a *Cannabis* oil. As used herein, a "*Cannabis* oil" is an extract formed by contacting at least a part of a *Cannabis* plant with an oil. The extracting oil may optionally be removed. Extracting oils may be selected from olive oil, sunflower oil, hemp oil, sesame oil, coconut oil, vegetable oil, canola oil, grape seed oil, almond oil, medium-chain triglyceride (MCT) oil, and any other edible oil, or a combination thereof.

The term "cannabinoid" as used herein relates to any molecule that has been isolated from a *Cannabis* plant or synthetically created to have activity involving the endocannabinoid system.

The term "cannabinoid fraction" is used to describe the combination of cannabinoid compounds present in the *Cannabis* extract.

The terms "terpenes" and "terpenoids" as used herein refer to a class of hydrocarbon molecules, which often provide a unique smell. Terpenes are derived from units of isoprene, which has the molecular formula $C_5H_8$. The basic molecular formula of terpenes are multiples of the isoprene unit, i.e. $(C_5H_8)_n$, where n is the number of linked isoprene units. Terpenoids are terpene compounds that have been further metabolised in the plant, typically through an oxidative process, and therefore usually contain at least one oxygen atom.

The term "terpene fraction" is used to describe the combination of terpene and terpenoid compounds present in the *Cannabis* extract.

The inventors have observed that the efficacy of a pharmaceutical composition is enhanced when the terpene fraction has a certain profile, i.e. a certain proportion of particular terpenes/terpenoids are present in the extract. It is believed that the increase in efficacy may be synergistic (i.e. non-additive). It is also believed that the presence of specific components in the terpene fraction may enhance the patient's tolerance to cannabinoid therapy.

In some embodiments, the *Cannabis* extract contains high amounts (e.g., greater than 50% by weight) of a main cannabinoid, typically THC. In some embodiments, the *Cannabis* extract may comprise the cannabinoid fraction in an amount of about 50% to about 99.999% by weight, for example, about 55% to about 99.999%, about 60% to about 99.999%, about 70% to about 99.999%, about 80% to about 99.999%, about 90% to about 99.999%, about 90% to about 99.99%, about 90% to about 99.9%, or about 90% to about 99.5% by weight of the *Cannabis* extract. In some embodiments, the *Cannabis* extract comprises about 0.001% to about 50% by weight of non-cannabinoids, for example, about 0.001% to about 20% by weight or about 0.001% to about 10% by weight non-cannabinoids.

In some embodiments, the cannabinoid fraction is present from about 0.001 to about 60% by weight of the pharmaceutical composition, for example, about 5% to about 55% or about 10% to about 50% by weight of the pharmaceutical composition. In some embodiments, the pharmaceutical formulation consists of the *Cannabis* extract.

In some embodiments, one or more additional compounds (e.g., cannabinoid, terpene or terpenoid compounds) may be added to the *Cannabis* extract. The addition of the one or more additional compounds may compensate for natural variations in the relative amounts of certain compounds being expressed in the *Cannabis* plant. The added compounds may be synthetic versions of the desired compounds, they may be purified compounds obtained from other *Cannabis* extracts, or they may be added by blending two or more extracts.

To date, over 100 cannabinoids have been identified in *Cannabis* extracts. A comprehensive list of these cannabinoids may be found in Mahmoud A. El Sohly and Waseem Gul, "Constituents of *Cannabis Sativa.*" In *Handbook of Cannabis* Roger Pertwee (Ed.) Oxford University Press (2014) (ISBN: 9780199662685). Cannabinoids that have been identified in *Cannabis* extracts include: Cannabigerol (E)-CBG-C5, Cannabigerol monomethyl ether (E)-CBGM-C5 A, Cannabigerolic acid A (Z)-CBGA-C5 A, Cannabigerovarin (E)-CBGV-C3, Cannabigerolic acid A (E)-CBGA-C5 A, Cannabigerolic acid A monomethyl ether (E)CBGAM-C5 A and Cannabigerovarinic acid A (E)-CBGVAC3A); (±)-Cannabichromene CBC-C5, (±)-Cannabichromenic acid A CBCA-C5 A, (±)-Cannabivarichromene, (±)-Cannabichromevarin CBCV-C3, (±)-Cannabichromevarinic acid A CBCVA-C3 A); (−)-Cannabidiol CBD-C5, Cannabidiol momomethyl ether CBDMC5, Cannabidiol-C4 CBD-C4, (−)-Cannabidivarin CBDVC3, Cannabidiorcol CBD-C1, Cannabidiolic acid CBDA-C5, Cannabidivarinic acid CBDVA-C3); Cannabinodiol CBNDC5, Cannabinodivarin CBND-C3); $\Delta^9$-Tetrahydrocannabinol $\Delta^9$-THC-C5, $\Delta^9$-Tetrahydrocannabinol-C4 $\Delta^9$-THCC4, $\Delta^9$-Tetrahydrocannabivarin $\Delta^9$-THCV-C3, $\Delta^9$-Tetrahydrocannabiorcol, $\Delta^9$-Tetrahydrocannabinolic acid $\Delta^9$-THCA-C5 A, $\Delta^9$-Tetrahydrocannabinolic acid B, $\Delta^9$-THCA-C5 B, $\Delta^9$-Tetrahydrocannabinolic acid-C4 A and/or B $\Delta^9$-THCA-C4 A and/or B, $\Delta^9$-Tetrahydro-cannabivarinic acid A $\Delta^9$-THCVA-C3 A, $\Delta^9$-Tetrahydrocannabiorcolic acid A and/or B $\Delta^9$-THCOA-C1 A and/or B), (−)-$\Delta^8$-trans-(6aR,10aR)-$\Delta^8$-Tetrahydrocannabinol $\Delta^8$-THC-C5, (−)-$\Delta^8$-trans-(6aR,10aR)-Tetrahydrocannabinolic acid A $\Delta^8$-THCA-C5 A, (−)-(6aS,10aR)-$\Delta^9$-Tetrahydrocannabinol (−)-cis-$\Delta^9$-THC-C5); Cannabinol CBN-C5, Cannabinol-C4 CBN-C4, Cannabivarin CBN-C3, Cannabinol C2 CBN-C2, Cannabiorcol CBN-C1, Cannabinolic acid A CBNA-C5 A, Cannabinol methyl ether CBNM-C5, (−)-(9R,10R)-trans-Cannabitriol (−)-trans-CBT-C5, (+)-(9S,10S)-Cannabitriol (+)-trans-CBT-C5, (±)-(9R,10S/9S,10R)-); Cannabitriol (±)-cis-CBT-C5, (−)-(9R,10R)-trans-10-O-Ethyl-cannabitriol (−)-trans-CBT-OEt-C5, (±)-(9R,10R/9S,10S)-Cannabitriol-C3 (±)-trans-CBT-C3, 8,9-Dihydroxy-$\Delta$6a(10a)-tetrahydrocannabinol 8,9-Di-OH-CBT-C5, Cannabidiolic acid A cannabitriol ester CBDA-C5 9-OH-CBT-C5 ester, (−)-(6aR,9S,10S,10aR)-9,10-Dihydroxyhexahydrocannabinol, Cannabiripsol, Cannabiripsol-C5, (−)-6a,7,10a-Trihydroxy-$\Delta^9$-tetrahydrocannabinol (−)-Cannabitetrol, 10-Oxo-$\Delta$6a (10a)tetrahydrocannabinol OTHC); (5aS,6S,9R,9aR)-Cannabielsoin CBE-C5, (5aS,6S,9R,9aR)-C3-Cannabielsoin CBE-C3, (5aS,6S,9R,9aR)-Cannabielsoic acid A CBEA-C5 A, (5aS,6S,9R,9aR)-Cannabielsoic acid B CBEA-C5 B; (5aS,6S,9R,9aR)-C3-Cannabielsoic acid B CBEA-C3 B, Cannabiglendol-C3 OH-iso-HHCV-C3, Dehydrocannabifuran DCBF-C5, Cannabifuran CBF-C5), (−)-Δ$^7$-trans-(1R, 3R,6R)-Isotetrahydrocannabinol, (±)-Δ$^7$-1,2-cis-(1R,3R,6S/1S,3S,6R)-Isotetrahydrocannabivarin, (−)-Δ$^7$-trans-(1R,3R, 6R)-Isotetrahydrocannabivarin; (±)-(1aS,3aR,8bR,8cR)-Cannabicyclol CBL-C5, (±)-(1aS,3aR,8bR,8cR)-Cannabicyclolic acid A CBLA-C5 A, (±)-(1aS,3aR,8bR, 8cR)-Cannabicyclovarin CBLV-C3; Cannabicitran CBTC5; Cannabichromanone CBCN-C5, Cannabichromanone C3 CBCN-C3, and Cannabicoumaronone CBCON-C5.

The *Cannabis* extract may comprise 0.005-99% by weight of a main cannabinoid based on the total weight of the extract, for example, from 0.005-90%, 0.005-65%, 0.005-40%, 0.005-10%, 0.005-2%, 0.005-0.1%, 0.005-0.05%, 0.01-0.05%, 0.01-99%, 0.01-90%, 0.01-10%, 0.01-2%, 0.01-0.1%, 0.01-0.05%, 0.015-0.03% 5-90%, 10-90%, 20-90%, 25-85%, 50-99%, 40-90%, 50-90% or 55-85% by weight based on the total weight of the extract. The main cannabinoid may be Δ$^9$-tetrahydrocannabinol (THC). In some embodiments, the *Cannabis* extract comprises the main cannabinoid in an amount of 5-90%, 10-90%, 20-90%, 25-85%, 50-99%, 55-95%, 70-95%, 75-95% or 80-90% by weight of the cannabinoid fraction. Typically, the *Cannabis* extract further comprises one or more secondary cannabinoids. Cannabidiol (CBD) and/or cannabinol (CBN) may also be present in the *Cannabis* extract as secondary cannabinoids. Typically, each secondary cannabinoid is present in an amount from about 0.001% to about 30% by weight of the cannabinoid fraction, for example, from 0.001-10%, 1-10%, 2-10%, 3-5% or 8-10% by weight based on the total weight of the cannabinoid fraction. Other cannabinoids may also be present, but typically these do not form part of the active ingredients.

The pharmaceutical composition may comprise THC in a concentration of about 1 mg/ml to about 100 mg/ml, for example, from about 5 mg/ml to about 50 mg/ml, about 5 mg/ml to about 30 mg/ml, about 10 mg/ml to about 30 mg/ml or about 18 mg/ml to about 22 mg/ml.

In some embodiments, the *Cannabis* extract comprises 0.001-20% by weight of cannabidiol (CBD) as a secondary cannabinoid, for example, from 0.0001-20%, 0.001-10%, 1-20% or 1-10% by weight of the extract or cannabinoid fraction. The pharmaceutical composition may comprise CBD in a concentration of about 0.5 mg/ml to about 10 mg/ml, for example, from about 0.5 mg/ml to about 5 mg/ml, about 0.5 mg/ml to about 2.5 mg/ml or about 0.9 mg/ml to about 1.1 mg/ml.

The ratio by weight of THC to CBD may be from 10:1 to 50:1, for example from 10:1 to 30:1, 15:1 to 25:1 or about 20:1.

In some embodiments, the *Cannabis* extract comprises 0.0001-20% by weight of cannabiniol (CBN), for example, from 0.001-20%, 0.001-10%, 1-20% or 1-10% by weight of the extract or cannabinoid fraction. The pharmaceutical composition may comprise CBN in a concentration of about 0.5 mg/ml to about 10 mg/ml, for example, from about 0.5 mg/ml to about 5 mg/ml, about 1 mg/ml to about 5 mg/ml or about 1.8 mg/ml to about 2.2 mg/ml.

The ratio by weight of THC to CBN may be from 5:1 to 20:1, for example from 5:1 to 15:1 or about 10:1.

The ratio by weight of CBN:CBD may be from about 1:1 to about 10:1, for example from about 1:1 to about 5:1, about 1.5:1 to about 3:1 or about 2:1.

Typically, the *Cannabis* extracts also comprise other cannabinoids in addition to THC, CBN and CBD. These cannabinoids include Δ$^9$-Tetrahydrocannabinolic acid (THCA), (−)-Cannabidivarin (CBDV) and Cannabigerol (CBG). Each of these cannabinoids may be present in an amount from 0.001% to 30% by weight of the extract or cannabinoid fraction.

In some embodiments, certain cannabinoids may be absent, or present in non-detectable amounts (e.g., less than 0.001% by weight of the analyte). In some embodiments, the *Cannabis* extract may exclude (or comprise in an amount of less than or equal to 0.5% by weight of the cannabinoid fraction) one or more of the following cannabinoids: Δ$^9$-Tetrahydrocannabivarin (THCV), Cannabidiolic acid (CBDA), Cannabigerolic acid (CBGA) and (−)-Cannabidivarin (CBDV).

The *Cannabis* extract comprises a non-cannabinoid fraction, which typically includes a terpene fraction. The terpene fraction comprises terpenes and terpenoids. The *Cannabis* extract comprises a terpene fraction in an amount of at least about 3% by weight of the extract, for example, at least about 3.5%, 4%, or 4.5% by weight. In some embodiments, the *Cannabis* extract comprises a terpene fraction in an amount of less than 50% by weight, for example, less than 45%, 40%, 35%, 30%, 25%, 20%, 15%, 10%, 9%, 8%, 7%, 6%, 5%, or 4% by weight of the extract. In some embodiments, the *Cannabis* extract comprises about 3% to about 50% by weight of terpene and terpenoid compounds, for example, about 3% to about 20% by weight, about 3% to about 10% by weight, about 3% to about 6% by weight or about 3 to about 5% by weight of the extract or composition.

The ratio by weight of the cannabinoid fraction to the terpene fraction may be from about 8:1 to about 33:1, for example, from about 10:1 to about 30:1, about 10:1 to about 25:1 or about 15:1 to about 25:1. In some embodiments, the ratio by weight of the main cannabinoid to the terpene fraction may be from about 5:1 to about 30:1, for example, about 10:1 to about 25:1 or about 15:1 to about 20:1.

Typically, the terpene fraction in the plant material used to form the extract may have a different terpene/terpenoid profile than the terpene profile of the final extract, both in terms of the amounts of specific compounds in the terpene fraction and the weight of the terpene fraction relative to the other components. For example, a *Cannabis* flower may comprise about 20% by weight cannabinoids and about 3% by weight terpenes, corresponding to a ratio of cannabinoid fraction:terpene fraction of about 20:3 (about 7:1). Following extraction and concentration (i.e., removal of the extractant), the amount of cannabinoids may increase to about 50-90% by weight and the terpene fraction may amount to about 0.1-6% by weight of the *Cannabis* extract, corresponding to a significant increase in the ratio of cannabinoid fraction:terpene fraction. This typical scenario shows that while the cannabinoids are concentrated when the extractant is removed, the relative amount of the terpene fraction is reduced, likely due to the volatility of many of the terpenes/terpenoids present in the terpene fraction. Therefore, the profile of the terpene fraction present in the *Cannabis* extract is significantly different from the profile of the terpene fraction that exists in Nature.

A variety of terpenes and terpenoids have been identified in *Cannabis* extracts, including monoterpenes, monoterpenoids, sesquiterpenes and sesquiterpenoids. For example, the following terpenes and terpenoids have been identified in *Cannabis* extracts: Alloaromadendrene, allyl hexanoate, benzaldehyde, (Z)-a-cis-bergamotene, (Z)-a-trans-bergamotene, β-bisabolol, epi-a-bisabolol, β-bisabolene, borneol (camphol), cis-y-bisabolene, borneol acetate (bornyl acetate), α-cadinene, camphene, camphor, cis-carveol, caryophyllene (β-caryophyllene), α-humulene (α-caryophyllene), γ-cadinene, Δ-3-carene, caryophyllene oxide, 1,8- cineole, citral A, citral B, cinnameldehyde, α-copaene (aglaiene), γ-curcumene, β-cymene, β-elemene, γ-elemene, ethyl decdienoate, ethyl maltol, ethyl propionate, ethylvanillin, eucalyptol, α-eudesmol, β-eudesmol, γ-eudesmol, eugenol, cis-β-farnesene ((Z)-β-farnesene), trans-α-farnesene, trans-β-farnesene, trans-γ-bisabolene, fenchone, fenchol (norbomanol, β-fenchol), geraniol, αc-guaiene, guaiol, methyl anthranilate, methyl salicylate, 2-methyl-4-heptanone, 3-methyl-4-heptanone, hexyl acetate, ipsdienol, isoamyl acetate, lemenol, limonene, d-limonene (limonene), linolool (linalyl alcohol, β-linolool), α-longipinene, menthol, γ-muurolene, myrcene (β-myrcene), nerolidol, trans-nerolidol, nerol, β-ocimene (cis-ocimene), octyl acetate, α-phellandrene, phytol, α-pinene (2-pinene), β-pinene, pulegone, sabinene, cis-sabinene hydrate (cis-thujanol), β-selinene, α-selinene, γ-terpinene, terpinolene (isoterpine), terpineol (α-terpineol), terpineol-4-ol, α-terpinene (terpilene), α-thujene (origanene), vanillin, viridiflorene (ledene), and α-ylange.

It is believed that the presence of the particular terpenes/terpenoids in the terpene fraction is associated with beneficial effects of the pharmaceutical composition in use.

The terpene fraction typically comprises beta-myrcene. It is believed that beta-myrcene enhances the bioavailability of the cannabinoids present in the extract and/or assists in allowing the cannabinoids to pass the blood-brain-barrier. Beta-myrcene may be present in an amount of from 0% to about 40% by weight of the extract. In some embodiments, beta-myrcene is present in an amount of about 0-50% by weight of the terpene fraction, for example, from about 0.001% to about 45%, about 0.001% to about 25%, 5.1% to 29%, about 5.5% to about 25%, about 20% to about 50%, about 20% to about 45% or about 30% to about 45% by weight of the terpene fraction. In some embodiments, the pharmaceutical composition comprises beta-myrcene in a concentration of up to about 10 mg/ml, for example, up to about 5 mg/ml, about 1 mg/ml or about 0.5 mg/ml.

In some embodiments, the ratio by weight of THC to beta-myrcene may be from 20:1 to about 55:1, for example, from about 30:1 to about 50:1 or from about 35:1 to about 45:1.

The terpene fraction may further comprise one or more of linalool and nerolidol.

Linalool is a terpenoid that is found in many flower and spice plants having the molecular formula $C_{10}H_{18}O$. It is believed that when linalool is present in a *Cannabis* extract, it provides a sedative effect. In some embodiments, linalool may be present in an amount of at least 0.05% by weight of the terpene fraction. In some preferred embodiments, linalool is present in an amount of 0-50% by weight of the terpene fraction. In other embodiments, linalool is present in amount of from about 0.05% to 50% by weight of the terpene fraction, for example, from about 0.1% to about 20%, about 0.05 to about 25%, about 0.001% to about 45%, about 0.001% to about 25%, about 20% to about 50%, about 20% to about 45% or about 30% to about 45% by weight of the terpene fraction. In some embodiments, the pharmaceutical composition comprises linalool in a concentration of up to about 10 mg/ml, for example, up to about 5 mg/ml, about 1 mg/ml or about 0.5 mg/ml.

In some embodiments, the ratio by weight of THC to linalool may be from 20:1 to about 55:1, for example, from about 30:1 to about 50:1 or from about 35:1 to about 45:1.

Nerolidol is a sesquiterpenoid having the molecular formula of $C_{15}H_{16}O$. It exists in Nature in two isomeric forms, namely nerolidol 1 and nerolidol 2, which differ in the geometry around a central olefin, i.e., either cis or trans isomers. The extract may comprise nerolidol (i.e., both nerolidol 1 and nerolidol 2) in an amount of at least 0.001% by weight of the terpene fraction, for example, from about 0.01% to about 30% or 0.01% to 20% by weight of the terpene fraction. Typically, nerolidol 1 is present in greater amount relative to nerolidol 2. In some embodiments, nerolidol 1 may be absent (or present in an amount below the limit of detection). In some embodiments, nerolidol 2 may be absent (or present in an amount below the limit of detection). In some embodiments, nerolidol 1 and nerolidol 2 are absent (or present in an amount below the limit of detection). Nerolidol 1 may be present in the extract in an amount of at least about 0.001% by weight of the terpene fraction, for example, from 0.001% to 20% or 0.001 to 15% by weight of the terpene fraction. Nerolidol 2 may be present in the extract in an amount of at least about 0.001% by weight of the terpene fraction, for example, from 0.001% to 20% or 0.001 to 15% by weight of the terpene fraction. In some embodiments, the pharmaceutical composition comprises nerolidol in a concentration of up to about 5 mg/ml, for example, up to about 3 mg/ml, about 1 mg/ml or about 0.25 mg/ml.

In some embodiments, the ratio by weight of THC to nerolidol may be from 50:1 to about 100:1, for example, from about 60:1 to about 95:1 or from about 70:1 to about 90:1.

The terpene fraction may also comprise beta-caryophyllene. Beta-caryophyllene may be present in an amount of at least 0.001% by weight of the terpene fraction, for example, from 0.001% to 20% or 0.001% to 15% of the terpene fraction. In some embodiments, the pharmaceutical composition comprises beta-caryophyllene in a concentration of up to about 1 mg/ml, for example, up to about 0.5 mg/ml or about 0.25 mg/ml.

In some embodiments, the extract further comprises humulene. It is believed that that humulene enhances the sedative properties of the extract. Humulene is also sometimes called alpha-caryophyllene. In some embodiments, the pharmaceutical composition comprises humulene in a concentration of up to about 1 mg/ml, for example, up to about 0.5 mg/ml or about 0.25 mg/ml.

In some embodiments, the *Cannabis* extract further comprises ocimene. Ocimene may be present in an amount of at least 0.001% by weight of the terpene fraction, for example, from 0.001% to 20% or 0.001% to 5% by weight of the terpene fraction. In some embodiments, the pharmaceutical composition comprises ocimene in a concentration of up to about 1 mg/ml, for example, up to about 0.5 mg/ml or about 0.25 mg/ml.

In some embodiments, the terpene fraction comprises beta-myrcene, linalool and nerolidol 1. The ratio by weight of beta-myrcene to linalool may be about 1:1 (e.g. from 1:2 to 2:1). The ratio by weight of beta-myrcene to nerolidol may be about 2:1 (e.g., from 1:1 to 3:1). The ratio by weight of linalool to nerolidol may be about 2:1 (e.g., from 1:1 to 3:1). In some embodiments, the ratio by weight of beta-myrcene:linalool:nerolidol is about 2:2:1.

In some embodiments, the terpene fraction may be present in the composition in an amount from 3% to 6% by weight of the extract and may comprise:
   beta-myrcene in an amount of from 0% to 50% by weight of the terpene fraction;
   linalool in an amount of from 0% to 50% by weight of the terpene fraction;
   nerolidol 1 in an amount of from 0% to 20% by weight of the terpene fraction; and nerolidol 2 in an amount of from 0% to 20% by weight of the terpene fraction.

In some embodiments, specific terpenes or terpenoids may be absent, or present in non-detectable amounts (e.g., less than 0.001% by weight of the analyte or less than or equal to 0.5 mg/ml of the pharmaceutical composition). In some embodiments, one or more of the following terpenes or terpenoids are absent, or present in non-detectable amounts: alpha-pinene, beta-pinene, limonene, p-cymene, camphene, alpha-terpinene, gamma-terpinene, delta-s-carene, terpinolene, isopulegol, geraniol, and guaiol.

The amounts of cannabinoids can be determined by high-performance liquid chromatography (HPLC), including ultra performance liquid chromatography (UPLC) and amounts of terpenes can be determined by HPLC and/or gas chromatography (GC). It will be appreciated that, as for all plant extracts, the amount of each component in the *Cannabis* extract may vary in some cases by +/−10%, +/−25% or +/−50%. In some embodiments, the amount of a cannabinoid and/or a terpene may be determined by UPLC using a Waters Acquity UPLC system equipped with a Waters photodiode array detector (PDA) or detection by mass spectrometry. Using UPLC the limit of quantitation (LoQ) of THC, CBD and/or CBN or related substances may be less than 1 µg/ml, for example, the LoQ of CBD may be ≤0.086 µg/ml, CBN may be ≤0.038 µg/ml and/or THC may be ≤0.089 µg/ml may be detected in an analyte. Accordingly, in some embodiments, the pharmaceutical compositions comprise CBD in an amount greater than 0.086 µg/ml, CBN in an amount greater than 0.038 µg/ml and/or THC in an amount greater than 0.089 µg/ml.

The *Cannabis* extract is preferably free of toxins associated with plant extracts. For example, preferably the *Cannabis* extract is free of aflatoxins (such as aflatoxin B1, B2, G1 and G2), mycotoxins (such as ochratoxin A), heavy metals (such as arsenic, cadmium, lead and mercury) and pesticides. In some embodiments, the pharmaceutical composition comprises less than 4 µg/ml total aflatoxins and/or less than 2 µg/ml aflatoxin A. In some embodiments, the pharmaceutical composition may comprise less than 20 µg/ml ochratoxin. In some embodiments, the pharmaceutical composition comprises ≤0.3 ppm arsenic, ≤0.5 ppm cadmium, ≤5 ppm lead and/or ≤0.5 ppm mercury.

In some embodiments, the pharmaceutical composition may comprise not more than 20% by weight total ash.

The pharmaceutical composition may further comprise one or more pharmaceutically acceptable carriers, diluents, adjuvants, excipients or any combination thereof.

The term "pharmaceutical composition" relates to a composition comprising at least one active ingredient that is in a pharmaceutically acceptable form. The term "pharmaceutical composition" may encompass compositions intended to be sold as nutraceutical products (e.g. supplements that provide a health benefit). In some embodiments, the pharmaceutical composition is a nutraceutical composition.

The pharmaceutical composition may comprise the *Cannabis* extract in a maximum amount of up to 99 wt % of the pharmaceutical composition, for example, up to 95 wt %, 90 wt %, 85 wt %, 80 wt %, 75 wt %, 70 wt %, 65 wt %, 60 wt %, 55 wt %, 50 wt %, 45 wt %, 40 wt %, 35 wt %, 30 wt %, 25 wt %, 20 wt %, 15 wt %, 10 wt %, 5 wt %, 4 wt %, 3 wt %, 2 wt %, 1 wt % or lower. The minimum amount of *Cannabis* extract in the pharmaceutical compositions may be at least 0.001 wt %, 0.005 wt %, 0.01 wt %, 0.05 wt %, 0.1 wt %, 0.5 wt %, 1 wt %, 5 wt %, 10 wt %, 15 wt %, 20 wt %, 25 wt %, 30 wt %, 35 wt %, 40 wt %, 45 wt %, 50 wt % or higher. The pharmaceutical compositions may comprise the *Cannabis* extract in amount between any of these minimum and maximum amounts, such as 0.001 wt % to 99 wt %, 0.1 wt % to 65 wt % or 1 wt % to 50 wt %. In some embodiments, the one or more pharmaceutically acceptable carriers, diluents, adjuvants, excipients or any combination thereof provides the balance of weight of the pharmaceutical composition.

The carrier, diluent, adjuvant and/or excipient are "pharmaceutically acceptable" meaning that they are compatible with the other ingredients of the composition and are not deleterious to a subject upon or following administration. The pharmaceutical compositions may be formulated, for example, by employing solid or liquid vehicles or diluents, as well as pharmaceutical additives of a type appropriate to the mode of desired administration (for example, excipients, binders, preservatives, stabilisers, flavours, etc.) according to techniques such as those well known in the art of pharmaceutical formulation (See, for example, Remington: The Science and Practice of Pharmacy, 21st Ed., 2005, Lippincott Williams & Wilkins). The pharmaceutically acceptable carrier may be any carrier included in the United States Pharmacopeia/National Formulary (USP/NF), the British Pharmacopoeia (BP), the European Pharmacopoeia (EP), or the Japanese Pharmacopoeia (JP). In some embodiments, the carrier, diluent, adjuvant and/or excipient may be non-natural (e.g., synthetically produced).

The pharmaceutical composition includes those suitable for oral, sublingual, buccal, rectal, nasal, topical, vaginal or parenteral (including intramuscular, subcutaneous and intravenous) administration or in a form suitable for administration by inhalation or insufflation.

The *Cannabis* extract, together with a conventional adjuvant, carrier, excipient or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the *Cannabis* extract described herein, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, dispersions, suspensions, and emulsions, for example, a pharmaceutically acceptable oil, water or water-propylene glycol solutions. For example, a sublingual preparation can be prepared in a carrier comprising a pharmaceutically acceptable oil, and parenteral injection liquid preparations can be formulated as solutions in aqueous polyethylene glycol solution.

Sterile liquid form compositions include sterile solutions, suspensions, emulsions, syrups and elixirs. The *Cannabis* extract can be suspended in a pharmaceutically acceptable carrier, such as sterile water, sterile organic solvent or a mixture of both.

Other liquid form preparations include those prepared by combining the *Cannabis* extract with one or more oils (e.g., an essential oil) or waxes. An "essential oil" is an oil extracted from a material, such as a plant material (e.g., steam extraction, or contacting the plant material with an extractant) or pressing, which contains primarily hydrophobic, and generally fragrant, components of the plant material. Suitable oils and waxes include Sesame oil, Olive oil, Sunflower oil, Arnica essential oil, Lavender essential oil, Lavender Spike essential oil, Frankincense essential oil, Lemongrass essential oil, Cinnamon Leaf essential oil, Rosemary Cineole essential oil, Rosemary essential oil, Bergamot essential oil, Myrrh essential oil, Sage essential oil, Coconut oil, Bees wax and Hemp oil.

The pharmaceutical compositions may be formulated for parenteral administration (e.g., by injection, for example bolus injection or continuous infusion) and may be presented in unit dose form in ampoules, pre-filled syringes, small volume infusion or in multi-dose containers optionally with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g., sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the *Cannabis* extract in the required amount in the appropriate carrier with various other ingredients such as those enumerated above, as required, followed by sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile suspension of the active ingredient plus any additional desired ingredients.

The active ingredients may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active may be incorporated with excipients and used in the form of ingestible tablets, buccal tablets, troches, capsules, elixirs, suspensions, syrups, wafers, and the like.

The amount of active ingredient in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

In some embodiments, the pharmaceutical composition is formulated for sublingual administration. Sublingual administration relates to administration of a formulation under the tongue of a subject. In some instances, sublingual administration may be considered to be a form of oral administration or topical administration. Sublingual administration may be considered a form of oral administration as the formulation is taken "by mouth" and in some instances, after application under the tongue, the subject may swallow the formulation which may allow for at least a portion of the active ingredients to be absorbed through the digestive tract. Subligual administration may be considered a form of topical administration as it may include administration of the active ingredient(s) in the formulation through the mucus membrane under the tongue. Formulations suitable for sublingual administration include tablets (e.g. dissolvable, dispersible, effervescent and multi-purpose tablets), strips, drops, sprays, lozenges and combinations thereof.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well-known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the active ingredients may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier may form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of a sleep disorder.

Also described herein are compositions absent a carrier where the compositions are in unit dosage form. Accordingly, also provided is a medicament comprising the *Cannabis* extract.

In some embodiments, the pharmaceutical composition further comprises an active agent other than the *Cannabis* extract. Any suitable active agent may be used provided that the activity of the active agent and/or the *Cannabis* extract is not diminished when combined.

Methods of Treatment

In another aspect, also provided is a method for treating a sleep disorder. The method comprising administering to a patient in need thereof an effective amount of the pharmaceutical composition described herein.

The pharmaceutical compositions may be used to treat a sleep disorder. Sleep disorders are described in the International Classification of Sleep Disorders (ICDS). ICDS-3 was published in 2014 and characterises sleep disorders as belonging to one of the following classes: (1) Insomnias; (2) Sleep Related Breathing Disorders; (3) Central Disorders of Hypersomnolence; (3) Circadian Rhythm Sleep-Wake Disorders; (4) Parasomnias; (5) Sleep Related Movement Disorders. Accordingly, the sleep disorders to be treated by the pharmaceutical composition may include any sleep disorders from the classes (1) Insomnias; (2) Sleep Related Breathing Disorders; (3) Central Disorders of Hypersomnolence; (3) Circadian Rhythm Sleep-Wake Disorders; (4) Parasomnias; (5) Sleep Related Movement Disorders. In particular, the pharmaceutical compositions may be effective in the treatment of a sleep disorder selected from: insomnia, narcolepsy, hypersomnia, sleep apnoea, periodic limb movement disorder, restless legs syndrome, nocturnal eating (drinking) syndrome, jet lag, shift work sleep disorder, irregular sleep-wake pattern, confusional arousals, sleepwalking, sleep terrors, sleep talking, nightmares, sleep paralysis, REM sleep behaviour disorder, snoring, sleeping sickness, a sleep disorder associated with another disease or condition, or any other sleep disorder.

By "effective amount" it is meant an amount sufficient that when administered to the patient an amount of the drug is provided to achieve an effect. In the case of a therapeutic method, this effect may be the treatment of the sleep disorder. Therefore, the "effective amount" may be a "therapeutically effective amount". By "therapeutically effective amount" it is meant an amount sufficient that when administered to the patient an amount of drug is provided to treat the disease or a symptom of the disease.

In some embodiments, the methods comprise administration of THC in an amount from 1 mg/day to 50 mg/day, for example, from 5 mg/day to 40 mg/day, 5 mg/day to 30 mg/day, 5 mg/day to 25 mg/day or 10 mg/day to 20 mg/day. In some embodiments, the methods may comprise administering THC in an amount of 10 mg/day or 20 mg/day. The methods may comprise administering CBD in an amount from 0.001 mg/day to 10 mg/day, for example, from 0.01 mg/day to 10 mg.day or 0.1 mg/day to 5 mg/day. In some embodiments, the methods may comprise administering CBD in an amount of 1 mg/day. The methods may comprise administering CBN in an amount from 0.001 mg/day to 10 mg/day, for example, from 0.01 mg/day to 10 mg.day or 0.1 mg/day to 5 mg/day. In some embodiments, the methods comprise administering CBN in an amount of 1 mg/day or 2 mg/day. The methods may comprise administering THC, CBD and/or CBN in any combination of these daily dosage amounts. The pharmaceutical compositions preferably comprise amounts of THC, CBD and CBN suitable for administration of any of these daily dosage amounts.

As used herein, the terms "treating", "treatment", "treat" and the like mean affecting a subject, tissue or cell to obtain a desired pharmacological and/or physiological effect. The effect may be prophylactic in terms of completely or partially preventing, or reducing the severity of, a disease or associated symptom, and/or may be therapeutic in terms of a partial or complete cure of a disease. A reference to "treating" a sleep disorder therefore encompasses: (a) assisting the patient to fall asleep; (b) assisting the patient remain asleep once sleep has been achieved; (c) relieving or ameliorating the effects of the sleep disorder, e.g. enhancing wakefulness during non-sleep periods; or (d) preventing the sleep disorder from occurring in a subject predisposed to, or at risk of, the sleep disorder, so that the sleep disorder does not develop or occur in the subject, or develops in a less severe form.

In some embodiments, the sleep disorder is insomnia. Symptoms and severity of insomnia may be measured by the Insomnia Severity Index (ISI) questionnaire. Typically the ISI is administered by a clinician, nurse or researcher or may be self-administered by the patient. The ISI assesses both night-time and daytime components of insomnia and is available in several languages. The ISI asks seven questions each to be scored on a scale of 0-4 relating to (1) the difficulty in falling asleep, (2) difficulty staying asleep, (3) problems waking too early, (4) satisfaction relating to current sleep patterns, (5) perception as to how noticeable the sleep problem may be to others, (6) degree of concern regarding the sleep problem, and (7) the extent to which the sleep problem interferes with daily functioning. The methods may provide an improvement in one or more of these seven aspects of insomnia. In some embodiments of the methods of treatment, the patient to be treated may have an initial ISI score of 7 or more, in some cases, the initial ISI score may be 10 or more. In some embodiments, a method of treating insomnia may provide a reduction of the ISI score of the patient relative to an initial ISI score. This reduction in ISI score may be by 1, 2, 3, 4, 5, 6 or more units on the ISI scale, and preferably results in the patient having an ISI score of 7 or less after treatment.

The ISI may be used alone to assess the severity of the patient's insomnia or it may be used together with one or more other questionnaires, such as quality of life enjoyment and satisfaction questionnaire (Q-les-Q), work and social adjustment scale (WSAS), depression anxiety stress scale (DASS) questionnaire, dysfunctional beliefs about sleep (DBAS) questionnaire, multidimensional fatigue inventory questionnaire, and any other recognised questionnaire known in the field.

Typically the patient is assessed by one or more questionnaires prior to receiving treatment and then at regular intervals (e.g. an interval of 1, 2, 3, 4, 5, 6, 7 or 8 weeks) during the course of treatment. The assessment during treatment may begin 2 weeks after commencement of treatment.

In some embodiments, the treatment may be maintained for up to 14 days, for example, the treatment may be maintained for 1, 2, 3, 4, 5, 6, 7, 8, 9, 10, 11, 12, 13 or 14 days. In some embodiments, the treatment is maintained for longer than 14 days, for example, for 3 weeks, 1, 2, 3, 4, 5, 6, 12, 18, 24, 36 months or longer.

Typically, the pharmaceutical composition is administered once daily preferably a short time before the patient attempts to sleep. In some embodiments, the pharmaceutical composition is administered within about 2 hours of the patient attempting to sleep, for example, within about 1.5 hours, within about 1 hour or within about 30 minutes prior to sleep.

In some embodiments, the administration is sublingual administration. In such embodiments, the pharmaceutical composition may be presented as sublingual drops.

In some embodiments, the insomnia may be assessed by measuring one or more objective measures of sleep. Objective measures of sleep may be measured by polysomnography (PSG) and/or actigraphy. The objective measures of sleep may include measuring: Sleep Onset Latency (SO); Wake After Sleep Onset (WASO); Total Sleep Time (TST); Sleep Efficiency (SE); REM versus NREM sleep patterns including slow-wave sleep patterns and percentage of time in all sleep stages; sleep apnea; periodic limb movements; and combinations thereof. In some embodiments, a method of treating insomnia may provide an improvement in one or more objective measures of sleep, for example, 2, 3, 4, 5, 6 or more of the objective measures of sleep.

The patient in need of therapy for insomnia may be any patient suffering from insomnia, for example, as assessed by ISI. However, in some embodiments, not all patients may be suitable. For example, in some embodiments, a patient who satisfies one or more of the following factors may be excluded:

a. Untreated cardiovascular disease, arrhythmias (other than well controlled atrial fibrillation), hypertension or severe heart failure: or
b. History of allergies particularly to plant-based products containing terpenes. ie flavours and aromatic natural oils for example citrus, mango, lavender, thyme, cedarwood and pine products: or
c. Known hypersensitivity to cannabinoids: or
d. Currently regularly using (on 3 or more nights/days per week) psychotropic or CNS-active drugs, such as *Cannabis*, opioids, benzodiazepines: or
e. Inability to refrain from use of psychotropic or CNS-active drugs (including *Cannabis*. opioids, benzodiazepines) for at least one week prior to treatment: or
f. Inability to refrain from use of Cytochrome P450 inhibitors for at least one week prior to treatment. Examples include macrolide antibiotics (erythromycin, clarithromycin), azole antifungals (itraconazole, ketoconazole, posaconazole, voriconazole), protease inhibitors (ritonavir, telaprevir, boceprevir), calcium channel blockers (amlopdipine), high cholesterol medication (gemfibrozil), cyclosporine, danazol, tachycardia medication (amiodarone), hypertension medication (verapamil diltiazem), niacin (vitamin B3>1 g/day), and/or grapefruit juice; or g. Untreated metabolic disorders such as diabetes; or h. Presence of severe depression, severe anxiety or other severe psychopathologic conditions based on self-report or depression scores on the DASS of 11 or greater or anxiety scores on the DASS of 8 or greater; or i. History of suicide attempt; or j. History of seizures or epilepsy; or k. History of drug or alcohol abuse; or l. Insomnia associated with sleep (AHI of 15 of greater events/hour) or movement disorders such as restless legs, periodic limb movement (PLM) (30 or greater events/hour or 5 or greater events/hour with associated PLM arousals); or m. Current practice of behavioural therapies to facilitate sleep; or n. Current *Cannabis* use (within 2 months prior to commencement of treatment); or o. Pregnancy or lactation; or p. Inability to refrain from 2 or more standard drinks/day of alcohol consumption; or q. Inability to refrain from 400 mg/day or more of caffeine consumption; or r. Shift workers or other workers and athletes who require testing and screening for *Cannabis* products as part of their employment; or s. Any person required to drive within 10 hours of dose, or those with a self-reported history of falling asleep while driving; or t. Current delayed sleep phase syndrome where wake up time is regularly later than 8.00 am.

The method may also comprise administering an active agent other than the *Cannabis* extract. This active agent may be administered simultaneously or consecutively with the *Cannabis* extract. By consecutively it is meant that each of the *Cannabis* extract and the other active agent are administered separately and may be at different times. Typically, when the *Cannabis* extract and the other active agent are administered consecutively they are administered within 24 hours, or within 12, 8, 6, 5, 4, 3, 2, or 1 hour(s) of each other. The *Cannabis* extract may be administered before or after the other active agent. Further, the route of administration for the *Cannabis* extract and the other active agent may be the same or different.

In another aspect, also provided is the use of the *Cannabis* extract in the preparation of a medicament for the treatment of the sleep disorder.

Also provided is a kit comprising in separate parts:

(a) an effective amount of the *Cannabis* extract; and (b) a pharmaceutically acceptable carrier, diluent, adjuvant, excipient or a combination thereof.

In some embodiments, the kit further comprises a part comprising (c) an effective amount of an active agent other than the *Cannabis* extract.

In another aspect, there is provided the pharmaceutical composition for treating the sleep disorder. The pharmaceutical composition may be any of the pharmaceutical compositions described above, comprising any above-described combination of components, provided that it comprises the *Cannabis* extract with the specified terpene fraction. The sleep disorder may also be any of those described above.

EXAMPLES

The invention will be further described by way of non-limiting examples. It will be understood to persons skilled in the art of the invention that many modifications may be made without departing from the spirit and scope of the invention.

Example 1—*Cannabis* Extracts

The following *Cannabis indica* 'bedita' extract formulation was produced:

THC—20 mg/ml, e.g. 18-22 mg/ml
CBN—2 mg/ml, e.g. 1-3 mg/ml
CBD—1 mg/ml, e.g. 0.5-1.5 mg/ml
Linalool—0.5 mg/ml (or less)
Myrcene—0.5 mg/ml (or less)
Nerolidol—0.25 mg/ml (or less)
Remaining plant material made up of other cannabinoids or other terpenes (less than 10% of Total or less than 15% of Total) wherein each other cannabinoid or terpene is present at low concentrations (e.g. <0.5%)

No alpha pinene and beta pinene was detected (<0.5%);

Limonene levels were low e.g. <0.2%.

THCV was at low levels 0.5%).

The formulation was completed using sunflower oil as the carrier oil.

Example 2—A Study to Evaluate the Efficacy of Sublingual Cannabinoid Based Medicine Extract Compared With Placebo for the Treatment of Sleep Disorders Due to Insomnia This study is a randomised double-blind placebo controlled cross-over study evaluating the efficacy of a medicinal *Cannabis* extract containing THC for improving sleep in people with insomnia. Efficacy is evaluated using subjective sleep quality measures using the standard Insomnia Severity Index, objective measures of sleep determined using PSG and actigraphy, and subjective measures of sleep outcome and quality of life using daily sleep diary and standard questionnaires for quality of life, mood, stress, anxiety, fatigue including Depression Anxiety Stress Scales (DASS). Dysfunctional Belief About Sleep (DBAS), Multidimensional Fatigue Inventory (MFI).

The primary aim of this study is to evaluate the efficacy of a sublingual cannabinoid extract (composition 1 of the present invention) containing delta-9-tetrahydrocannibinol (THC) for improving sleep in people with insomnia.

The secondary aim is to evaluate sleep quality and quality of life improvements in people with insomnia when using composition 1 of the present invention as compared with a placebo. A further secondary aim is to determine patient safety of composition 1 as measured by incidence of adverse events during course of the study.

Composition 1 comprises delta-9-tetrahydrocannibinol (THC) 20 mg/ml, cannabinol (CBN) 2 mg/ml and cannabidiol (CBD) 1 mg/ml as an extract of *Cannabis* plant with excipient sunflower oil. The sunflower oil is used as the excipient to stabilise the formulation including the cannabinoids and as a diluent of the plant extract.

Each dose is delivered sublingually with 0.5 ml cannabinoid extract (THC 10 mg, CBN 1 mg and CBD 0.5 mg).

Participants (between ages 25 and 70 years of age) male or female with chronic insomnia will be screened on Day 1 of the study.

Each qualifying subject admitted into the study meets all of the inclusion and none of the exclusion criteria. 24 participants are enrolled in the study. This study is conducted over 9-12 months. The study requires participants to spend 3 overnight stays in clinic at The University of Western Australia, Centre for Sleep Science. Participants will be required to take the Investigational Product for 2 weeks and placebo for 2 weeks at home.

This study conforms to the National Statement on Ethical Conduct in Human Research and meets the relevant requirements of the ICH Note for Guidance on Good Clinical Practice (CPMP/ICH-135/95) and the TGA.

Unless the context requires otherwise, all percentages referred to herein are percentages by weight of the pharmaceutical composition. Similarly, unless the context requires otherwise, all ratios referred to herein are ratios by weight.

Various features of the invention are described and/or claimed with reference to a certain value, or range of values. These values are intended to relate to the results of the various appropriate measurement techniques, and therefore should be interpreted as including a margin of error inherent in any particular measurement technique. Some of the values referred to herein are denoted by the term "about" to at least in part account for this variability. The term "about", when used to describe a value, preferably means an amount within ±25%, ±10%, ±5%, ±1% or ±0.1% of that value.

Various values are described in terms of their percentage relative to the total weight of (i) the pharmaceutical composition, (ii) *Cannabis* extract or (iii) fraction of the extract (e.g. the cannabinoid fraction or the terpene fraction). The percentages of components included in the *Cannabis* extract or a fraction thereof (e.g. the cannabinoid fraction or terpene fraction) are intended to denote the percentage by weight of the specified compound relative to the percentage by weight of the other compounds present in the extract or specified fraction, for example, absent the carriers, diluents, adjuvants and excipients or any combination thereof. For example, a pharmaceutical composition comprising a *Cannabis* extract comprising a terpene fraction in an amount of at least 3% by weight of the extract is intended to denote a pharmaceutical composition wherein the cumulative weight of terpenes and terpenoids is 3% by weight or more when compared to the cumulative weight of compounds present in the extract including cannabinoids, terpenes, terpenoids and extractant/residual extractant. Further, a *Cannabis* extract comprising THC in an amount of about 85% by weight of the cannabinoid fraction is intended to denote an extract comprising THC in an amount of 85% by weight relative to the cumulative weight of all cannabinoids present in the extract.

The terms "a", "an", "and" and/or "the" and similar referents in the context of describing the invention and the claims which follow are to be construed to cover both the singular and the plural, unless otherwise indicated herein or clearly contradicted by context.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method for treating insomnia in a human in need thereof comprising:
    administering to the human in need thereof a therapeutically effective amount of a pharmaceutical composition including a *Cannabis* extract and sunflower oil to effectively treat the insomnia in said human in need thereof,
    wherein the *Cannabis* extract is present in an amount of from 0.5% to 5% by weight of the composition and the sunflower oil is present in an amount of from 95% to 99.5% by weight of the composition, wherein the *Cannabis* extract includes a cannabinoid fraction and a terpene fraction;
    the cannabinoid fraction including:
    $\Delta^9$-Tetrahydrocannabinol (THC) in an amount in the range from 70% to 95% by weight of the *Cannabis* extract,
    Cannabidiol (CBD) in an amount in the range from 2% to 5% by weight of the *Cannabis* extract, and
    Cannabinol (CBN) in an amount in the range from 5% to 10% by weight of the *Cannabis* extract,
    wherein a weight ratio of CBN:CBD is in a range of from about 1:1 to about 10:1;
    the terpene fraction is present in an amount of from 3% by weight to 10% by weight of the *Cannabis* extract, and wherein the terpene fraction includes linalool and beta-myrcene; and
    wherein the amount of pharmaceutical composition administered provides:
    THC in an amount of from 5 mg/day to 25 mg/day;
    CBD in an amount of from 0.1 mg/day to 5 mg/day; and
    CBN in an amount of from 0.1 mg/day to 5 mg/day.

2. The method of claim 1, wherein the terpene fraction contains linalool in an amount of from about 20% to about 45% by weight of the terpene fraction.

3. The method of claim 1, wherein the terpene fraction contains beta-myrcene in an amount of from about 20% to about 45% by weight of the terpene fraction.

4. The method of claim 1, wherein the terpene fraction includes nerolidol.

5. The method of claim 1, wherein the pharmaceutical composition includes:
    THC at 18-22 mg/ml;
    Nat 1-3 mg/ml;
    CBD at 0.5-1.5 mg/ml;
    linalool at 0.5 mg/ml or less;
    beta-myrcene at 0.5 mg/ml or less;
    nerolidol at 0.25 mg/ml or less; and
    sunflower oil.

6. The method of claim 1, wherein the pharmaceutical composition is administered once per day.

7. The method of claim 1, wherein the pharmaceutical composition is administered within about 1.5 hours prior to sleep.

8. The method of claim 1, wherein the pharmaceutical composition is administered sublingually.

* * * * *